(12) United States Patent
Pusiol (10) Patent No.: US 7,719,267 B2
(45) Date of Patent: *May 18, 2010

(54) APPARATUS AND METHOD FOR REAL TIME AND REAL FLOW-RATES MEASUREMENTS OF OIL AND WATER CUTS FROM OIL PRODUCTION

(75) Inventor: Daniel J Pusiol, Córdoba (AR)

(73) Assignee: Spinlock SRL, Alta Gracia, Provincia De Cordoba (AR)

( * ) Notice: Subject to any disclaimer, the term of this patent is extended or adjusted under 35 U.S.C. 154(b) by 481 days.

This patent is subject to a terminal disclaimer.

(21) Appl. No.: 11/608,042

(22) Filed: Dec. 7, 2006

(65) Prior Publication Data

US 2007/0164737 A1 Jul. 19, 2007

(30) Foreign Application Priority Data

Jan. 11, 2006 (AR) ............................... P060100100

(51) Int. Cl.
*G01V 3/00* (2006.01)
*A61B 5/055* (2006.01)

(52) U.S. Cl. ...................... 324/303; 324/306; 324/321; 600/419

(58) Field of Classification Search ......... 324/300–322; 600/407–435; 382/128–131
See application file for complete search history.

(56) References Cited

U.S. PATENT DOCUMENTS

| | | | | |
|---|---|---|---|---|
| 2,968,761 A * | 1/1961 | Zimmerman et al. | ........ | 324/303 |
| 3,213,356 A * | 10/1965 | Brown et al. | ................ | 324/303 |
| 3,213,357 A * | 10/1965 | Brown et al. | ................ | 324/303 |
| 3,226,632 A * | 12/1965 | Brown et al. | ................ | 324/303 |
| 3,360,716 A * | 12/1967 | Bloom et al. | ................ | 324/303 |
| 3,360,717 A * | 12/1967 | Bloom et al. | ................ | 324/303 |
| 4,187,721 A | 2/1980 | Smith | | |
| 4,531,093 A | 7/1985 | Rollwitz et al. | | |
| 4,536,711 A | 8/1985 | King et al. | | |
| 4,785,245 A | 11/1988 | Lew et al. | | |
| 4,866,385 A | 9/1989 | Reichwein | | |
| 5,648,616 A | 7/1997 | Keel | | |
| 5,684,399 A * | 11/1997 | Bayer | .......................... | 324/306 |
| 6,046,587 A | 4/2000 | King et al. | | |
| 6,073,495 A | 6/2000 | Stadler | | |
| 6,268,727 B1 * | 7/2001 | King et al. | ................. | 324/306 |
| 6,287,272 B1 | 9/2001 | Brisken et al. | | |
| 6,452,390 B1 | 9/2002 | Wollin | | |
| 6,479,994 B1 * | 11/2002 | Hills et al. | ................. | 324/306 |
| 6,549,007 B1 * | 4/2003 | Hills et al. | ................. | 324/306 |
| 6,822,454 B2 * | 11/2004 | Peck et al. | ................. | 324/321 |

(Continued)

FOREIGN PATENT DOCUMENTS

EP         0 866 319         3/1998

OTHER PUBLICATIONS

A. Abragham, The Principles of Nuclear Magnetism, Oxford University Press, 1998.

*Primary Examiner*—Brij B. Shrivastav
*Assistant Examiner*—Tiffany A Fetzner
(74) *Attorney, Agent, or Firm*—Volpe and Koenig, P.C.

(57) ABSTRACT

A inventive flow-meter uses a measuring method which is based on the passage time of fluid molecules in a single sensor, without using any magnetic field gradient for the measurement of said fluid mean velocity. This method consists of the ultrafast irradiation of hydrogen nuclei from fluid molecules through pulses which are repeated every short time intervals, following a Carr-Purcell-Meiboom-Gill (CPMG) type sequence.

17 Claims, 8 Drawing Sheets

U.S. PATENT DOCUMENTS

| | | |
|---|---|---|
| 7,141,978 B2 * | 11/2006 | Peck et al. .................. 324/321 |
| 7,372,264 B2 * | 5/2008 | Akkurt et al. ............... 324/303 |
| 2004/0015332 A1 | 1/2004 | Martin et al. |
| 2005/0216196 A1 * | 9/2005 | Akkurt et al. ................. 702/6 |
| 2006/0020403 A1 | 1/2006 | Pusiol |
| 2006/0250130 A1 * | 11/2006 | Akkurt et al. ............... 324/303 |
| 2007/0164737 A1 * | 7/2007 | Pusiol ........................ 324/306 |
| 2008/0174309 A1 * | 7/2008 | Pusiol et al. ................ 324/306 |

* cited by examiner

APPARATUS AND METHOD FOR REAL TIME AND REAL FLOW-RATES MEASUREMENTS OF OIL AND WATER CUTS FROM OIL PRODUCTION

FIELD OF INVENTION

This invention relates to a method and apparatus for real time and real production volumes measurements of flow-rates and proportions of a complex fluid consisting of a multiple-component heterogeneous blend. Particularly, this invention applies to the separate measurement of flow-rates and relative proportions (or cuts) of oil and water in oil, water and gas heterogeneous blends, both at the production line (or vein) from oil wells and other ducts which distribute various types of fluids. Proposed method and instrument allow measurement of flow-rates of the individual components of the complex fluid in a non-invasive, non-destructive way, and regardless of the blend condition, i.e., for example, a blend consisting of separate phases of oil, water and gas o a single emulsion phase. This invention solves the problem of previous solutions, which are limited to total maximum flow-rates amounting to a few tens of cubic meters of fluid per day.

BACKGROUND

Components at the production line are very seldom found in pure state, as they rather form emulsions or heterogeneous blends which relative proportions change with time. Said condition is typically termed "multiphase". This particularity of the fluid to be measured prevents use of conventional flow-meters, which may only measure total fluid flow-rate, as they are unable of identifying proportions of each particular component. Measurement errors are generally important because, among other factors, passage of gas in non-homogeneous proportions instantaneously modifies rheological properties of the multiple phase. The most used method actually consists of deviating production towards a temporal storage tank, collecting said generally daily production and, once components have separated by the action of gravity, relative volumes are measured. This method poses multiple implementing problems, as:

a) due to several reasons, it is not possible to completely separate blend components, such reasons may include:

1. formation of a water-oil emulsion interface, which may amount to a significant volume in the storage tank; and 2. natural settlement always results in a certain quantity of water remaining in emulsion with oil b) even where both components could be adequately separated, devices used for interface measuring are difficult to implement, as, for example, it is not possible to establish water or oil levels by simple level inspection.

c) in fact, this technique only allows control of the individual production of each well on a monthly frequency at most.

As regards the real time application of measurement techniques in the oil production, special consideration should be given to the fact that gas tends to flow at higher speeds than liquid components. Thus, gas flow-rate measurements should be necessarily performed separately from liquid components, or else such flow velocity should be measured once all of the components of the blend are adequately mixed.

Other more sophisticated techniques have been invented which are based on different measuring principles. As an example we can mention the simple Venturi tube, the Coriolis principle, ultrasound, gamma rays measuring, and Magnetic Resonance (NMR).

The first technique is based on the measurement of the pressure difference existing between both ends of a tube with variable section. Measurements performed by means of this method strongly depend from the gas which is dispersed or bubbles within the blend. Further, this method does not discriminate the multiphase composition.

Coriolis's mass flow-meter is a mechanical design in which flow passage through a curved duct or other medium produces the vibration of mechanical parts thereof. Two or more vibration sensors are installed on the device, said sensors being positioned at a certain distance one from each other in the flow direction. Such flow produces vibrations at pre-established resonance frequencies which depend on the material and shape of said mechanical parts, but vary according to mass flow density (for more details see U.S. Pat. No. 4,187,721). It is also possible to derivate a phase difference between the resonance frequencies of both sensors, which angle, divided by the resonance frequency f, is proportional to the flow mass proportion (for more details see U.S. Pat. No. 5,648,616 or EP-A-866 319). As this method involves mechanical interactions, it is also strongly dependent on the fluid compressibility, which in turn strongly depends on the gas proportion, both that gas which is dissolved within the vein and that which bubbles through it.

Another design which does not exhibit moving mechanical parts is based on the ultrasound emission and reception in order to measure transit time of the fluid through the carrying vein. The time taken by the ultrasound wave in arriving to the receptor element since its emission and through the liquid flow, is proportional to the fluid speed within the carrying conduct. The fluid blend is obviously used as the coupling substance between the emitting crystal and the receptor. Here again, gas plays an essential role as regards the evaluation of measurement errors. On the one hand, bubbles break said coupling and introduce very important errors both as regards the propagation time of the acoustic signal and the attenuation of the sound wave. Even where bubbles are absent, compressibility of the liquid medium strongly depends from the quantity of gas dissolved therein, this being a variable which remarkably affects measurement process and result.

However, the Nuclear Magnetic Resonance principle allows both measurements to be done: i) determination of oil, gas and water proportions in the fluid blend, and ii) determination of the flow speed of said blend. There exist several patents which disclose methods—not necessarily selective as regards multiphase fluids—which use NMR analysis. Among them, the following can be mentioned: 1) Rollwitz et al., Method and Apparatus for Coal Analysis and Flow Measurements, U.S. Pat. No. 4,531,093; 2) King et al. Method and Apparatus for Measuring Flow in a Pipe of Conduit, U.S. Pat. No. 4,536,711, and 3) Reichwein, Consistency Measuring Device, U.S. Pat. No. 4,866,385.

Previous art devices designed for flow measuring and/or flow mapping are based on two widely known principles: 1) "time of flight" of saturated or unsaturated spins on the NMR spectrometer magnetic field; 2) on what is known as spatial codification of spins phase as they displace on a magnetic field gradient.

State of the art is completed with those patents which disclose specific methods for measuring flow-rate of multiphase fluids:

1. U.S. Pat. No. 4,785,245, entitled Rapid Pulse NMR Cut Meter describes a flow-meter which employs an NMR analysis in order to determine the fraction of one of the components of a multi-phase fluid flowing through a production line. NMR signal amplitude of a certain component is obtained by means of a pulse sequence which radio-frequency is adequate for the relative relaxation times between fluid components. This patent does not disclose a simultaneous method able to measure flow-rate of one of the phases which signal has separated. That is to say, it requires another device in order to measure flow velocity of said component.

2. U.S. Pat. No. 6,046,587, Measurements of Flow Fractions, Flow Velocities and Flow Rates of a Multiphase Fluid using NMR Sensing and U.S. Pat. No. 6,268,727, Measurements of Flow Fractions, Flow Velocities and Flow Rates of a Multiphase Fluid using ESR Sensing, both to J. D. King, Q. Ni and A. de los Santos, disclose a sensor which employs at least two NMR spectrometers or one NMR spectrometer and another ESR (Electronic Paramagnetic Resonance) one. Basic principle of measurement methodology is based on what is known as "time of flight" between both spectrometers. Such system of two spectrometers which separately measure residence time of each phase at the magnetic field is of unpractical and costly implementation; also, its application is difficult in the case of oil fields, which are generally subject to harsh climates. Another variant of said patents are those filed with the INPI (Argentine Industrial Property Institute) No. 010104816 (Oct. 12, 2001) and patent pending in USA 2004/0015332, by M. Ramia, D. J. Pusiol, C. A. Martin, E. Fried and R. Garnero. This case comprises a single electronic part which is shared by two sensing coils, operation principle being that already described, that is, flow velocity is measured through time of flight of water and oil molecules through the space between both sensing coils. This device exhibits the same restrictions as that involving two spectrometers: measurable flow-rate is substantially lower than 100 m$^3$/day for the total fluid.

3. Flow-meter with phase separation disclosed by U.S. Pat. No. 6,452,390, by E. Wollin, entitled Magnetic Resonance Analyzing Flow Meter and Flow Measuring Method, proposes a methodology and associated apparatus which implementation is simpler than those already described. This methodology uses pulsed magnetic fields gradients in order to modulate the spins (or protons) precession phase. That is to say that spatial codification is carried out by which is commonly known as Laboratory System. The problem with this method is that at the common displacement velocities of protons on the magnetic field, magnetic field gradients application is technologically difficult to apply, due to the fact that, in order to produce an adequate magnetic field gradient, it is necessary to include important currents which on/off times are generally relatively long. That is to say that this methodology is generally restricted to relatively small flow-rates measurements.

4. Another variant of said patents are those filed with the INPI under No. P040102415 on Jul. 8, 2004, and the pending US patent publication no. 2006/0020403, by SpinLock SRL and D. J. Pusiol. Said applications disclose a flow-meter and cut sensor comprising a single coil associated to slanted planar plates magnet which generates a constant magnetic field, along with a magnetic field gradient. Said application further discloses the application of a pre-polarization field for rapid fluids, which may be removed in the case of slow fluids. Said application also discloses a derivation device with electronic key which allows measurement of N sensors groups with a single electronic system. In said application, spatial codification of the resonant nuclei position is carried out through a linear gradient of the magnetic field at the place of the excitation/Magnetic Resonance detection coil, which is preferably generated by the slanted position of the polar faces of a permanent magnet. In the case of high flow velocities, said gradient must be increased in order to attain the necessary effectiveness of the spatial codification process of the NMR spectrum of those protons forming the moving complex fluid. Upon the increase of said magnetic field gradient the Magnetic Resonance signal broadens and thus deteriorates. The maximum flow-rate limit measurable by means of this invention is given by the maximum value of magnetic field gradient that may be applied to the fluid passing through the sensor tube before the signal deteriorates, preventing the precision required for the particular use.

The inventive flow-meter employs a measurement method which is based on the passing time of the fluid molecules at a single sensor, without using any magnetic field gradient for fluid velocity measurements. This method consists of the ultrafast irradiation of hydrogen nuclei belonging to said molecules through repeated pulses within short time intervals, following a CPMG type sequence (see, e.g. A. Abragham, *The Principles of Nuclear Magnetism*, Oxford University Press, 1998); thus, the temporal evolution of the NMR signal depends from the number of "refreshment" molecules appearing in the volume of the excitation/detection coil. In turn, for a given interval between excitation pulses, said number of refreshment molecules depends on the fluid velocity at the production line. This invention is based on the fact that there exists a region of the CPMG sequence in which the spin echoes amplitude following application of each radio-frequency pulse exhibits a linear variation with time. Quotient between the slope of said linear relation and origin ordinate is proportional to flow velocity, whereas the origin ordinate contains information which allows the determination of the proportion of the different elements comprising the complex fluid, which produce a detectable NMR signal.

In order to establish the relative proportions within the heterogeneous blend of the production fluid (we are preferably referring to oil, water and gas proportions), the production duct is first introduced through a spins pre-polarization magnetic module and then through a magnetic resonance sensor module. Length of said pre-polarization field and the velocity of the complex fluid establish a passage time of said flow which, along with the relaxation time $T_1$ of the spins species which form part of one of the components of the complex fluid, allows protons present in the complex fluid portion to attain a polarization sufficient to produce a magnetic resonance signal in the magnetic resonance sensor module. Polarization of a particular component on the pre-polarization field is selected by adjusting length thereof in such a way that its protons will attain enough polarization so as to provide a NMR signal. In order to select the Magnetic Resonance signal of the component exhibiting a longer relaxation time, there is added to the pre-polarization magnetic field a second field (temporarily pulsed), extending its action on the production vein. That is to say that, in this situation, ordinate at the origin of adjustment of the linear region of the echoes of the CPMG sequence, after a repeated pulses sequence, will now represent protons from two of the fluid components, each with higher and lower $T_1$. From the quantitative comparison of ordinates at the origin of both signals, one which is obtained with a shorter length of the pre-polarization field and the other obtained with longer spatial length for the application of the pre-polarization field, relative proportions, or cuts, of both components are obtained. Where the fluid bears a third component, an adequately arranged third magnetic field will be added.

Measurements are sequentially carried out and appropriately repeated in order to obtain an adequate signal-to-noise relation. Typically, measurement is completed in a few seconds.

Accordingly, this invention may be applied in all those cases involving complex fluids circulation, as for instance: Oil-Water, Mud from Mining Operations, Industrial Fluids, etc.

SUMMARY

Accordingly, it is an object of the present application an apparatus and method for measuring flow-rate and cut of oil production in real time and volumes, which comprises, mutually associated, a magnetic resonance sensor module, a pulsed pre-polarization magnetic module of variable length, a radio-frequency electronic module for magnetic resonance, a magnetic resonance digital module and a control computer.

Still another object of the present invention is a method for the direct measurement in real time and flow-rates of the proportion and flow-rate of the different components which form a multiple-component complex fluid, which method makes use of the above device, said method comprising the following steps:

a. activation of the first segment of the pre-polarization magnetic field in order to pre-polarize resonant nuclei of said multiple-component complex fluid during a time adequate regarding the spin-lattice relaxation time $T_1$ of said first selected component in order to establish proportion and flow-rate thereof;

b. transmission of radio-frequency pulses through a transmitter $T_x$ included in said radio-frequency electronic module, according to the CPMG pulses sequence;

c. emission of said radio-frequency pulses from said radio-frequency electronic module towards said magnetic resonance sensor module in order to excite said resonant nuclei of said complex fluid and generate a magnetic resonance signal (NMR) as a response to said emitted radio-frequency pulses;

d. reception of response signals at said sensor assembly;

e. emission of said signals in said sensor assembly, through said receiver $R_x$, included in said radio-frequency electronic module;

f. digitalization of said response signals received by an analog/digital converter which is included in said magnetic resonance digital module;

g. transference of said digitalized signals to said control computer; and h. activation of said second segment of said pre-polarization magnetic field in order to pre-polarize said resonant nuclei of said multiple-component complex fluid during a time appropriate as regards the value of said second shorter spin-lattice relaxation time $T_1$ of said selected second component for the determination of its proportion and flow-rate;

i. repetition of steps b) to h) in order to obtain adequate signals for their further mathematical analysis in order to obtain relative proportions and flow-rates of the different components of said complex fluid;

j. activation of said third segment of said pre-polarization magnetic field in order to pre-polarize said resonant nuclei of said multiple-component complex fluid during a time appropriate as regards the value of said third shorter spin-lattice relaxation time $T_1$ of said selected third component for the determination of its proportion and flow-rate;

k. repetition of steps b) to j) in order to obtain adequate signals for their further mathematical analysis in order to obtain relative proportions and flow-rates of the different components of said complex fluid;

l. repetition of said steps until all the measurable components are measured;

m. by means of adequate mathematical operations, processing of the obtained resonance signals in order to obtain proportion and flow-rate of each of the components of the complex fluid.

Still another object of the present invention is a sensor assembly, comprising said magnetic resonance sensor module and said pulsed pre-polarization magnetic module of variable length.

Still another object is an arrangement of production lines for multiple-components complex fluids which uses the above device, wherein each of the various production lines of multiple-components complex fluids bears one of said sensor assemblies fixedly mounted; or a single sensor assembly is fixedly mounted on an auxiliary production line towards which the different complex fluid production lines converge.

Still another object is to prevent sensitivity to flow-rate measurement from showing peculiar interference effects, by means of the neutralization of eventual shifts at the NMR frequency, due to changes of the $B_0$ value on account of environmental thermal effects.

Still another object of the present invention is measuring of velocities profiles within the volume of the complex fluid distribution pipe.

Still another object is that said sensors are fixed or movable.

BRIEF DESCRIPTION OF THE DRAWINGS

The invention shall be better understood when referring to the following figures.

DETAILED DESCRIPTION OF THE PREFERRED EMBODIMENTS

Figure 1:
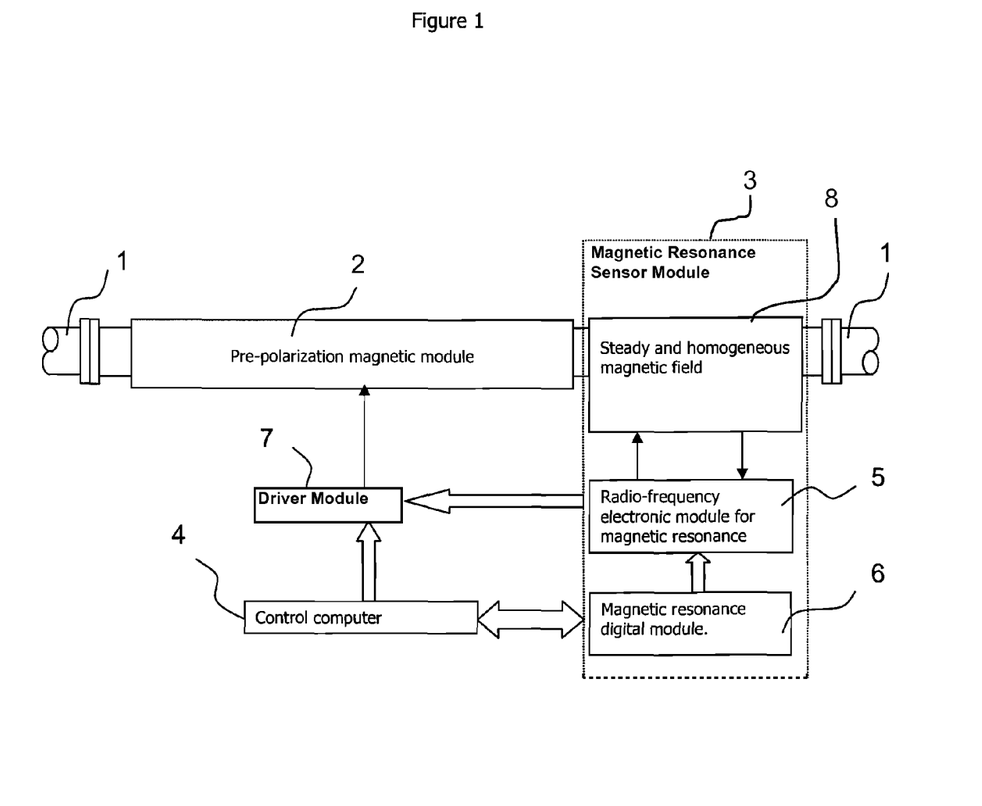
FIG. 1 illustrates a simplified block diagram of the preferred assembly according to the present invention.

FIG. 1 illustrates a simplified block diagram of the preferred assembly according to the present invention. Complex fluid circulates through production vein 1 and passes through a steady and homogenous magnetic field generated 8 generated at the pre-polarization Magnetic Module 2. Then, complex fluid passes through the Magnetic Resonance Sensor Module 3 through which the fluid is excited and its corresponding response signal is detected. Control Computer 4 is used for the synchronization of the complex fluid measurement process. Radio-Frequency Electronic Module for Magnetic Resonance 5 is used, on the one hand, in order to generate RF pulses used for exciting the complex fluid and on the other hand for the demodulation of the resonance signal from the fluid after the excitation. Magnetic Resonance Digital module 6 is used both for synthesizing pulses which modulate the RF produced at the Radio-Frequency Electronic Module for Magnetic Resonance 5 and for the digitalization of the signal demodulated at the Radio-Frequency Electronic Module for Magnetic Resonance 5. Length along which magnetic field is applied on the Pre-Polarization Magnetic Module is variable and may be adjusted by the Driver module 7.

Measurement of fluid mean velocity and phases proportion: the preferred method for measuring mean velocity of total fluid as well as the proportion of phases present in a multiphase fluid consists of the utilization of a pulses sequence known by the previous art as CPMG, with at least two phases producing a detectable NMR signal. Said sequence CPMG is a pulses sequence $\pi/2-\pi-\ldots-\pi$, so that magnetization which will be rotating on plan x-y (detection plan) will be constructed with those portions of the sample originally excited by the first pulse of the sequence (pulse of $\pi/2$) and which induce an electromotive force at the detection coil. Temporal origin of sequence (t=0) is defined as the instant in which the $\pi/2$ pulse application begins. During such short interval all of the fluid volume inside the detection coil is excited.

In order to better understand the invention, without loss of generality, analysis is restricted to the simplest case in which the fluid consists of two phases, for example one of them being formation water and the other oil; and further, wherein the production tube is completely full of fluid during the measuring process.

Thus, in t=0 total volume of fluid will be:

$$V_T(0) = V_A(0) + V_B(0) \tag{1}$$

wherein $V_A$ y $V_B$ are, respectively, the volume occupied by each of the two phases present in the fluid.

Where the fluid displaces at a mean velocity $V_1$, sample volume producing a detectable signal at time t will be:

$$V_T(t) = V_T(0) - Svt \tag{2}$$

wherein S is the cross-section of the detection (solenoidal) coil.

At time t the following equations should also be satisfied:

$$V_A(t) = V_A(0) - S_A vt = S_A(L - vt) \tag{3}$$

$$V_B(t) = V_B(0) - S_B vt = S_B(L - vt) \tag{4}$$

$$S_A + S_B = S \tag{5}$$

wherein $S_A$ and $S_B$ represent effective cross-sections corresponding to phases A and B respectively and L represents the length of detection coil.

By dividing equation (3) by equation (4) we have:

$$\frac{V_A(t)}{V_B(t)} = \frac{S_A}{S_B} \tag{6}$$

Previous equation evaluated at time t=0 and time t implies:

$$\frac{V_A(t)}{V_B(t)} = \frac{V_A(0)}{V_B(0)} \tag{7}$$

This means that in this approximation, at any time within the duration interval of the CPMG sequence, the relative volume proportions of both phases are equal to those existing at t=0 when the pulses sequence began. Thus, equations (3), (4) y (7) are easily deduced from the following expressions:

$$V_A(t) = V_A(0)\left(1 - \frac{v}{L}t\right) \tag{8}$$

$$V_B(t) = V_B(0)\left(1 - \frac{v}{L}t\right) \tag{9}$$

On the other hand, intensity of signal CPMG at time $t = n\tau$ (wherein $\tau$ is the separation between two consecutive $\pi$ pulses of the CPMG sequence), shall be given by the following expression:

$$I(v, t) = I_A(v, t)e^{-\frac{t}{T_{2eff}^A}} + I_B(v, t)e^{-\frac{t}{T_{2eff}^B}} \text{ wherein:} \tag{10}$$

$$I_\alpha(v, t) = M_\alpha(v) V_\alpha(t) = M_\alpha(v) V_\alpha(0)\left(1 - \frac{v}{L_{eff}}t\right) \tag{11}$$

In equation (11) $M_\alpha(v)$ represents magnetization by volume unit of component a circulating at a mean velocity v, $V_\alpha(0)$ is the volume of component $\alpha$ at the beginning of sequence CPMG (t=0), $T_{2eff}^\alpha$ is the effective spin-spin time of relaxation of component $\alpha$, v is the mean velocity of flow, and $L_{eff}$ represents the effective length of excitation coil.

By means of equation (11), equation 10 may be expressed as:

$$I(v, t) = \begin{bmatrix} M_A(v)V_A(0)e^{-\frac{t}{T_{2eff}^A}} + \\ M_B(v)V_B(0)e^{-\frac{t}{T_{2eff}^B}} \end{bmatrix} \left(1 - \frac{v}{L_{eff}}t\right) \tag{12}$$

Naturally, the expression (12) only has sense in those time t instants satisfying $0 \leq 1-(v/L)t \leq 1$.

Correction by pre-polarization factor: As the fluid is moving, in order to obtain a net magnetization which may be observed at the detection coil it is necessary to polarize it before it enters the excitation/detection coil. Typically this is achieved by placing an assembly of magnets along length $L_{pol}$ on the path immediately preceding the permanent magnet of the Magnetic Resonance module. Considering that the fluid moves at velocity v, the magnetization net fraction along direction z, perpendicular to flow direction, shall be given by the following equation:

$$f_\alpha(v, L_{pol}) = \frac{M_\alpha(v)}{M_\alpha(0)} = \left(1 - e^{-\frac{L_{pol}}{vT_1^\alpha}}\right) \tag{13}$$

Figure 2:
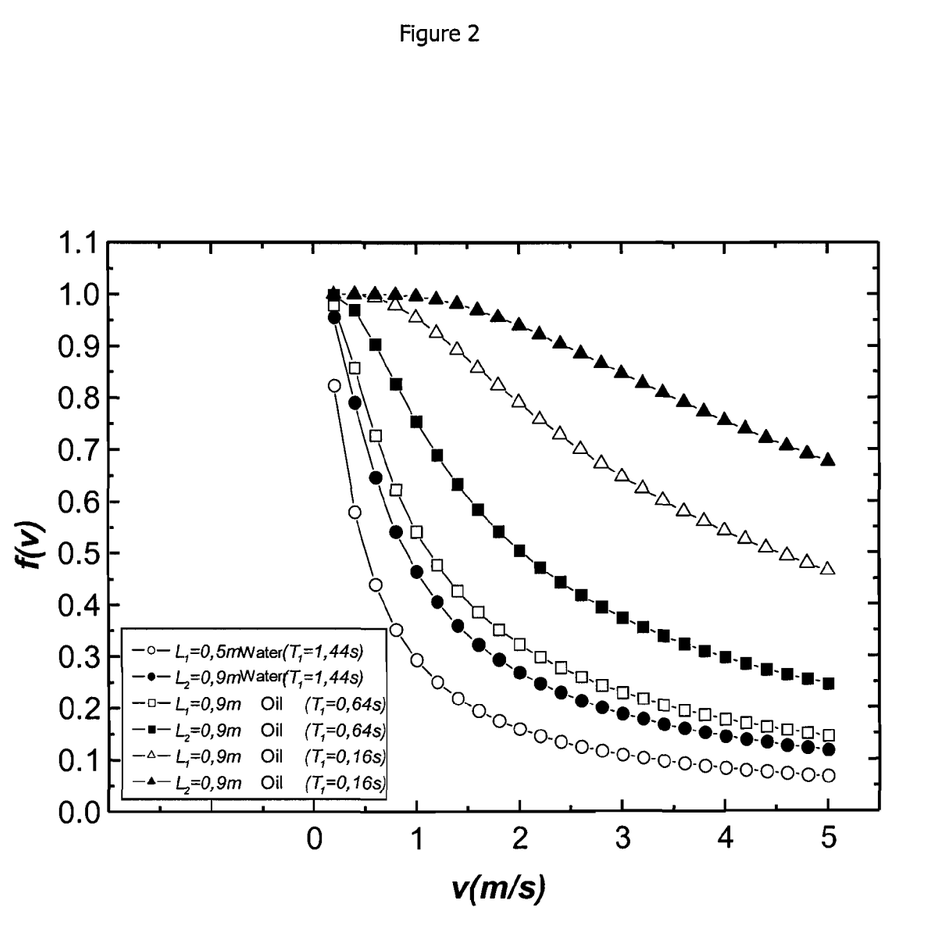
FIG. 2 illustrates the experimental behavior of the polarization factor f(v) in function of flow velocity v for two oil components ($T_1$=160 ms and $T_1$=640 ms) and formation water ($T_1$=1.44 s).
Figure 3:
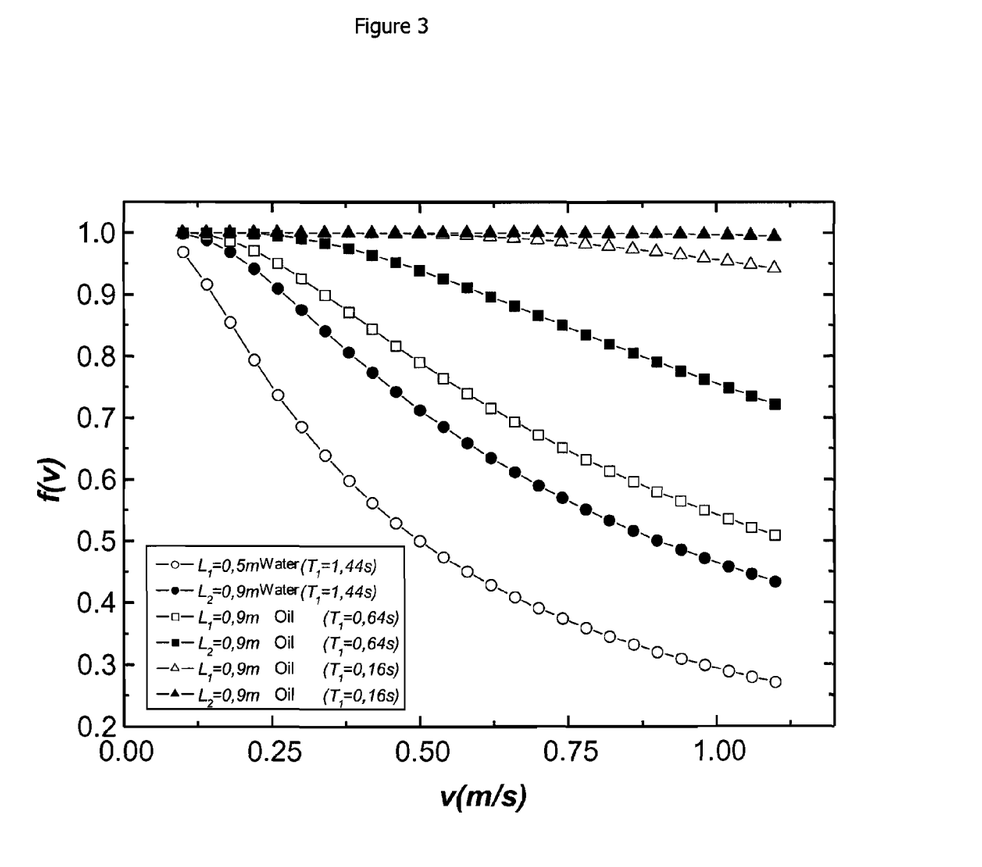
FIG. 3 illustrates behavior of polarization factor f(v) at the velocities v range comprised from 0.1 and 1.5 m/s for two oil components ($T_1$=160 ms and $T_1$=640 ms) and formation water ($T_1$=1.44 s).

Coefficient $f_\alpha(v)$ is named pre-polarization factor. FIG. 2 shows the typical behavior of $f_\alpha(v)$ in function of the velocity of the fluid for formation water ($T_1 = 1.4$ s) and two oil types ($T_1 = 160$ ms and $T_1 = 640$ ms) for polarization lengths $L_1 = 0.5$ m and $L_2 = 0.9$ m. FIG. 3 shows an enlargement of FIG. 2 at velocities from 0.1 to 1.5 m/s.

As can be seen in FIG. 3, the signal intensity at the end of the pre-polarization stage undergoes significant changes when using a pre-polarization stage of 50 cm or 90 cm long.

These changes are more noticeable in the case of those fluid components which relaxation times do not satisfy $L_{pol}/(vT_1) \ll 1$.

Taking into account the pre-polarization factor $f_\alpha(v)$, the expression (12) is finally transformed into:

$$I(v,t) = \begin{bmatrix} f_A(v)M_0^A V_A(0)e^{-\frac{t}{T^A_{2eff}}} + \\ f_B(v)M_0^B V_B(0)e^{-\frac{t}{T^B_{2eff}}} \end{bmatrix} \left(1 - \frac{v}{L_{eff}}t\right) \quad (14)$$

wherein $M_0^\alpha$ denotes $M_\alpha(0)$. Equation (14) and behavior of pre-polarization factors $f_\alpha(v)$, suggest two possible methods for approaching the problem of the simultaneous determination of the mean velocity of fluid and phase fractions present in a fluid of two phases.

Determination of fluid mean velocity: An important remark as regards equation (14) is that, in the case of values satisfying simultaneously conditions $t/T^A_{2eff} \ll 1$ and $t/T^B_{2eff} \ll 1$, said expression is reduced to:

$$I(v,t) = [f_A(v)M_0^A V_A(0) + f_B(v)M_0^B V_B(0)]\left(1 - \frac{v}{L_{eff}}t\right) \quad (15)$$

Expression (15) denotes that if we perform an adjustment of the amplitude of the echoes corresponding to the lineal region of the CPMG sequence, through an expression in the form of $I(v,t)=A+Bt$, quotient $B/A$ between slope and origin ordinate of adjustment is directly proportional to the mean velocity of fluid, proportionality constant being equal to the reciprocal of the effective length of the excitation/detection coil (antenna).

Determination of components Fraction with fixed length pre-polarization stage (Method 1). Expression 15 shows that for a given mean velocity v of fluid, the origin ordinate of adjustment of the region in which the CPMG signal intensity varies linearly, determines the sum of intensities due to the volume of each present phase, weighted with the polarization factors $f_\alpha(v)$ of each phase.

In some cases it is possible that the lineal approximation be invalid and thence adjustment of experimental data by means of expression (14) could be problematic due to the presence of two exponential functions. However, in such cases it is possible to use expression (14) bearing in mind that if separation $\tau$ between consecutive pulses of $\pi$ is much lower than $T^A_{2eff}$ and $T^B_{2eff}$ then:

$$I(v,\tau) \approx I(v,0) = I_0(v) = [f_A(v)M_0^A V_A(0) + f_B(v)M_0^B V_B(0)] = A(v)+B(v) \quad (16)$$

wherein $I(v,\tau)$ is the height of the first echo of the CPMG sequence. Thus, it is possible to adjust the following expression to the experimental data:

$$I(v,t) = \begin{bmatrix} A(v)e^{-\frac{t}{T^A_{2eff}}} + \\ (I(v,\tau) - A(v))e^{-\frac{t}{T^B_{2eff}}} \end{bmatrix}\left(1 - \frac{v}{L_{eff}}t\right) \quad (17)$$

Generally, exponentials present in equation (17) may be approached by the first terms of their Taylor development, which remarkably facilitates adjustment of expression (17) to experimental data.

In those cases in which the circulating fluid comprises two phases, e.g. oil and water, the origin ordinate of adjustment of the CPMG sequence through expressions (15) or (17) will be given by the following expression:

$$I_0(v) = x_p I_p^0(v) + (1-x_p)I_w^0(v) \quad (18)$$

wherein:

$x_p$: oil fraction
$I_p^0(v)$: origin ordinate for total oil content moving at velocity v
$I_w^0(v)$: origin ordinate for total water content moving at velocity v $$I_0(v) = x_p \underbrace{(I_p^0(v) - I_w^0(v))}_{C(v)} + \underbrace{I_w^0(v)}_{D(v)} \quad (19)$$

$$I(v) = x_p C(v) + D(v)$$

From expression (19) it can be clearly seen that for a given mean velocity v and that of the fluid, there exists a linear relation between the lineal adjustment origin ordinate and the oil fraction $x_p$ present in the fluid. Thence, if we perform an adjustment of the origin ordinate values for different known oil $x_p$ concentrations by means of expression (19) we may obtain coefficients $C(v)$ and $D(v)$. Once $C(v)$ and $D(v)$ are known, it is possible to obtain value of an unknown oil $x_p$ concentration through the expression:

$$x_p = (I(v)-D(v))/C(v) \quad (20)$$

Determination of components Fraction with variable length pre-polarization stage (Method 2). We will define coefficient $\gamma_\alpha(v)$ as the quotient of the pre-polarization factors of stage $\alpha$ circulating at mean velocity v, for two different lengths $L_1$ and $L_2$ of the pre-polarization stage:

$$\gamma_\alpha(v) = \frac{f_\alpha(v, L_2)}{f_\alpha(v, L_1)} = \frac{\left(1 - e^{-\frac{L_2}{vT_1^\alpha}}\right)}{\left(1 - e^{-\frac{L_1}{vT_1^\alpha}}\right)} \quad (21)$$

Alternatively using a pre-polarization stage of length $L_1$ and then another one of length $L_2$ we will see that, essentially, origin ordinates of the adjustments of each of the pulses sequences satisfy the following equations:

$$I_{01}(v) = I_{p1}(v) + I_{w1}(v) \quad (22)$$

$$I_{02}(v) = I_{p2}(v) + I_{w2}(v) \quad (23)$$

Also, the following relations are satisfied:

$$\begin{cases} \dfrac{I_{p2}}{I_{p1}} = \gamma_p(v) & (24) \\ \dfrac{I_{w2}}{I_{w1}} = \gamma_w(v) & (25) \end{cases}$$

Using rotations (24) and (25) and equations (22) and (23), we easily find that values of unknown quantities $I_{p1}$ and $I_{w1}$ correspond to:

$$I_{p1}(v) = \frac{\gamma_w(v)I_{01}(v) - I_{02}(v)}{(\gamma_w(v) - \gamma_p(v))} \quad (26)$$

$$I_{w1}(v) = \frac{\gamma_p(v)I_{01}(v) - I_{02}(v)}{(\gamma_p(v) - \gamma_w(v))}$$

Once calibration values of $I_p^O(v)$ and $I_w^O(v)$ are known when each of the phases is separately moving at a mean velocity v within a full duct, we are able to calculate absolute flow-rates of oil and formation water circulating through the pipe in the presence and absence of gas, air or a mixture thereof.

Figure 4:
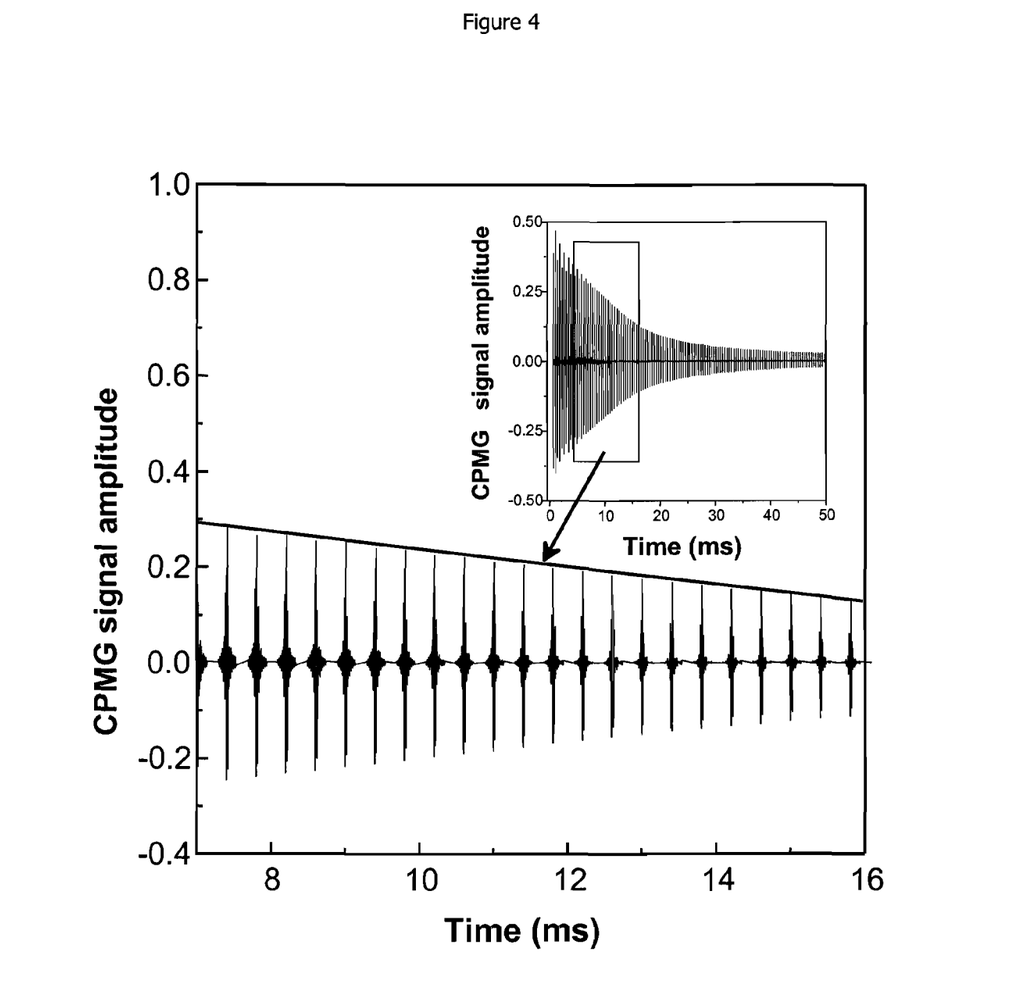
FIG. 4 shows the succession of echoes obtained upon the application of the CPMG sequence, for oil circulating at a velocity of 1.1 m/s.

FIG. 4 illustrates a typical CPMG sequence for pure oil circulating at a velocity of 1.1 m/s. Insert of said figure shows the region of the CPMG sequence which was enlarged at the bottom of FIG. 4. It may be clearly appreciated that echoes amplitude varies in a linear fashion at the beginning of the CPMG sequence, where ($t/T_{2eff} \ll 1$) is satisfied.

Figure 5:
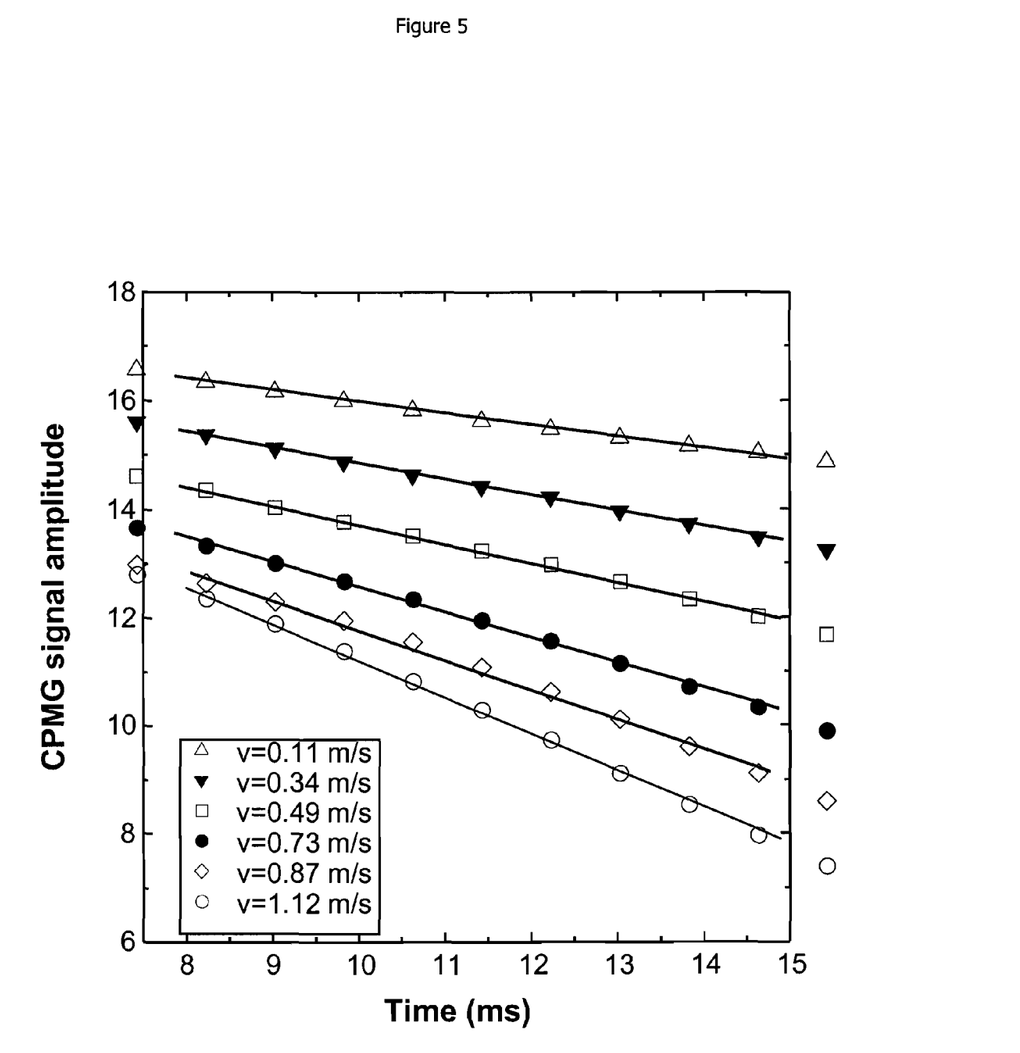
FIG. 5 illustrates amplitudes of the Fourier Transforms of CPMG sequences echoes for oil circulating at different velocities.

FIG. 5 shows amplitudes of FFT of CPMG sequences echoes performed for various flow velocities. It is clearly observed that FFT amplitudes follow a linear behavior. Also, slope of these lines clearly responds to the fluid total velocity.

Figure 6:
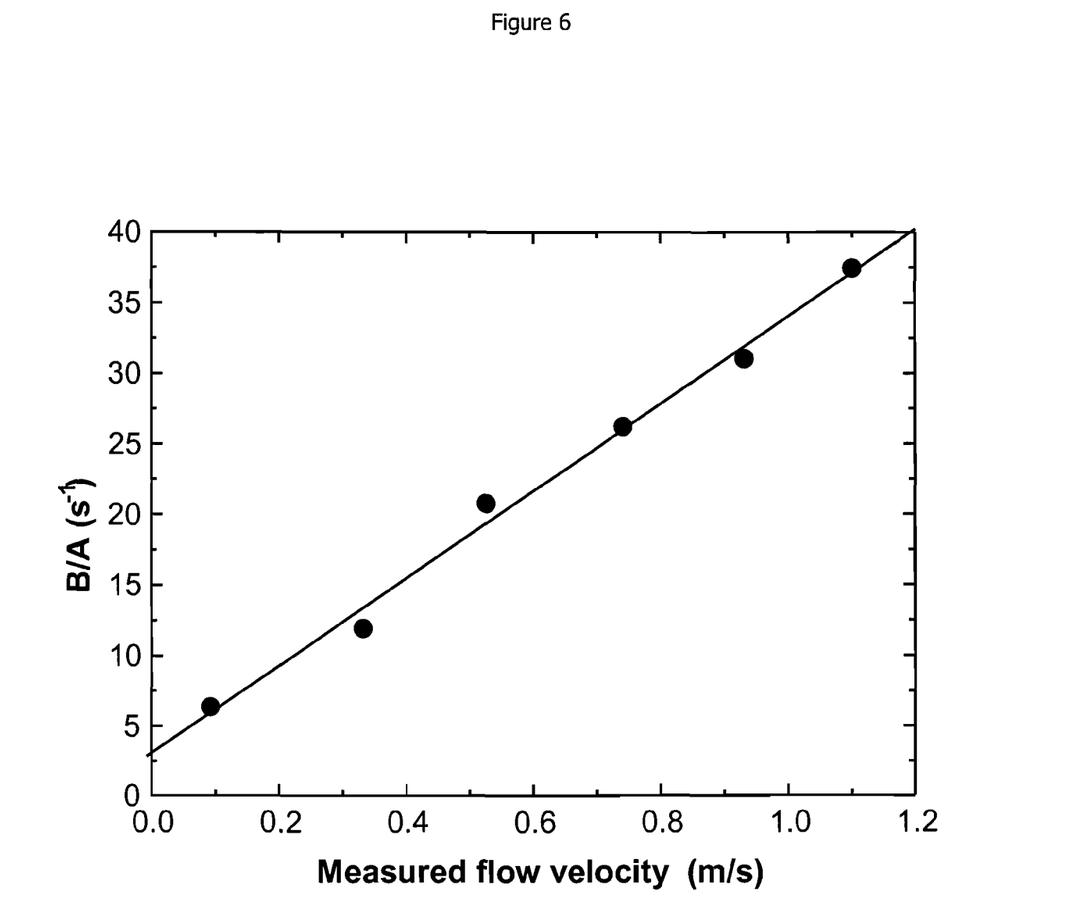
FIG. 6 shows dependence quotient B/A, between slope (B) and origin ordinate (A) of linear adjustments of CPMG sequences, in function of the experimentally established mean velocity of fluid.

FIG. 6 shows dependency of the B/A quotient between slope (B) and the origin ordinate (A) from linear adjustments of CPMG sequences in function of the fluid velocity, this velocity having been experimentally established. It can be clearly observed a linear dependency between both magnitudes.

Determination of Oil and Water Content of a Two-phases Blend

Figure 7:
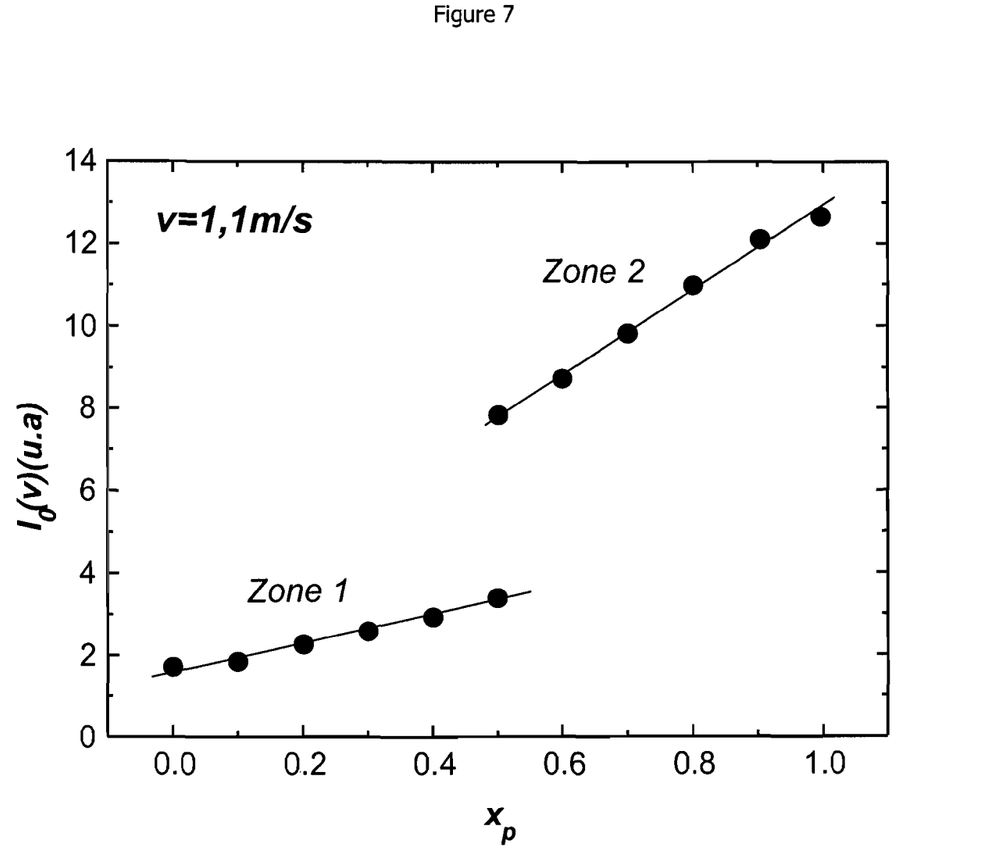
FIG. 7 illustrates experimental behavior of origin ordinates of linear adjustments of CPMG sequences for fluids comprised of different concentrations of oil and water circulating at a mean velocity of 1.1 m/s in function of oil concentration $x_p$.

Method 1. Fixed pre-polarization stage: FIG. 7 shows a graphic of the behavior of origin ordinates of linear adjustments of CPMG sequences in function of the oil $x_p$ concentration, by means of expression (15). Two zones are clearly observed. One for concentrations $x_p$ lower than 0.5, named zone 1, and another for concentrations higher than said value, named zone 2. It was experimentally established that pulse widths of π/2 (t) for each zone are different, namely 9 μs for zone 1 and 20 μs for zone 2.

Determination of the zone corresponding to the fluid which components fraction is to be measured may be easily done by means of de comparison of relative amplitudes of the first echo of two CPMG sequences, one with a pulse width of $t_w$=9 and the other with a pulse width of $t_w$=20 μs.

From the linear adjustment of each zone there can be obtained coefficients $C_i$ and $D_i$ (i=1,2) which characterize the relation between A and $x_p$.

$$A(v) = C_i(v)x_p + D_i(v) \tag{28}$$

After plotting a calibration curve as that shown by FIG. 7, for different total flow velocities, v, coefficients $C_i$ and $D_i$ are known and the oil fraction present in the fluid (and accordingly also that of water) is obtained though the following expression:

$$x_p = (A(v) - D_i(v))/C_i(v) \tag{29}$$

Figure 8:
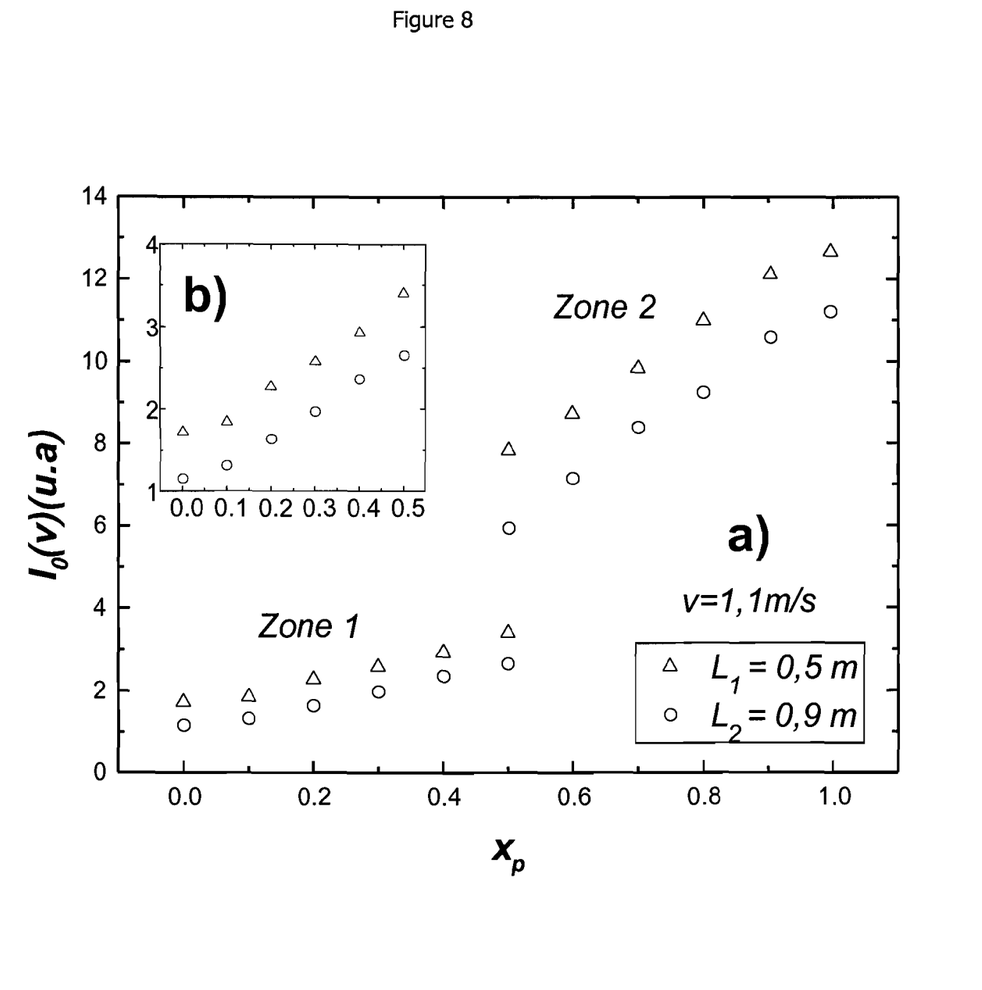
FIG. 8 illustrates experimental behavior of origin ordinates of linear adjustments of CPMG sequences for fluids comprised of different concentrations of oil and water circulating at a mean velocity of 1.1 m/s in function of oil concentration $x_p$, for two different lengths of the pre-polarization stage, $L_1$=0.5 m and $L_2$=0.9 m.

Method 2: variable pre-polarization stage: This method consists of the acquisition of two CPMG sequences with different lengths of the pre-polarization stage. There follows an adjustment of each of the sequences through expressions (14), (15) or (17) as the case may be and the origin ordinates $I_{01}(v)$ and $I_{02}(v)$ are obtained, which correspond to pre-polarization lengths $L_1$ and $L_2$, respectively. FIG. 8 shows typical behavior of origin ordinates ($I_0(v)$) of the adjustments of sequences CPMG through expression (15), for two different lengths of the pre-polarization stage ($L_1$=0,5 m (circles) and $L_2$=0,9 m (triangles)), in function of the concentration of oil $x_p$ for a fluid comprising oil and formation water. For a given oil $x_p$ concentration two different intensity values are observed, wherein the highest value corresponds to the highest pre-polarization length used.

On the other hand, we obtain effective coefficients $\gamma\gamma_\alpha^{eff}(v)$ from the experimental behavior of the coefficient of origin ordinates $I_{02}^\alpha(v)/I_{01}^\alpha(v)$, for each of the NMR detectable phases circulating separately, with full pipe, in function of mean velocity v. In such conditions, the following equations are satisfied:

$$I_{01}(v) = I_{p1}(v) + I_{w1}(v) \tag{30}$$

$$I_{02}(v) = I_{p2}(v) + I_{w2}(v) \tag{31}$$

$$\begin{cases} \dfrac{I_{p2}}{I_{p1}} = \gamma_p^{eff}(v) \tag{32} \\ \dfrac{I_{w2}}{I_{w1}} = \gamma_w^{eff}(v) \tag{33} \end{cases}$$

By using relations (30) and (31) and equations (32) and (33) we can easily find that unknown values of $I_{p1}$ and $I_{w1}$ correspond to:

$$I_{p1}(v) = \frac{\gamma_w^{eff}(v)I_{01}(v) - I_{02}(v)}{(\gamma_w^{eff}(v) - \gamma_p^{eff}(v))} \tag{26}$$

$$I_{w1}(v) = \frac{\gamma_p^{eff}(v)I_{01}(v) - I_{02}(v)}{(\gamma_p^{eff}(v) - \gamma_w^{eff}(v))} \tag{27}$$

Knowing calibration values $I^o_p(v)$ and $I^o_w(v)$ when each of the phases is separately circulating at a mean velocity v through a full pipe, we may calculate absolute flow-rates of the two phases moving through such pipe, both in the presence of gas, air or a mixture thereof, or otherwise.

The above description refers to the measurement of mean velocity at the production duct. In order to establish the flow regime at the production line, it is necessary to measure the velocity profile of the fluid components on the plane perpendicular to flow direction. To such end, the NMR signal of each component of the fluid is selectively excited. As usual, selective excitation is performed through a magnetic field gradient along said plane which is transversal to flow and the excitation of the respective NMR signals through frequency-selective pulses. The magnetic field gradient shall be essentially confined to the volume occupied by the radio-frequency coil of the magnetic resonance sensor module and may be linear or radial to such plane. Selective radio-frequency pulses at the excitation frequency are amplitude- and/or phase-modulated, preferably through a "sync" function. Once the CPMG sequence with excitation spatial selection is applied, velocity of the fluid component, excited to a certain resonance frequency, is obtained.

A preferred arrangement refers to the determination of the velocities profile in a cylindrical section tube. The magnetic field at the Magnetic Resonance sensor module should bear a radial field gradient at the plane transversal to flow direction. Selective excitation will provide, for each CPMG measurement, mean velocity at a transversal ring which diameter will depend on the magnetic field value and the resonant excitation frequency. This procedure is repeated for different values of the excitation frequency. Any person with average skill in the art may design and implement a device to be added to the flow-meter in order to perform the determination of the velocities profile directly in the production tube.

Whenever it says that an apparatus of this invention comprises, includes, contains, bears, is composed or consists of certain components, it should be understood, unless otherwise stated, that one or more components of those explicitly described may be present in the apparatus. In an alternative arrangement, however, the inventive apparatus may be described as essentially consisting of said components, wherein components of said arrangement which may materially alter the operation principle or distinctive features of the apparatus might not be included in the description of said alternative arrangement. In another alternative arrangement, the inventive apparatus may be described as consisting of certain components while other components of said arrangement might not be described.

The invention claimed is:

1. An apparatus configured for the real time and real volume measuring of flow-rate and cut of the production of a complex fluid, comprising a magnetic resonance sensor module, a pulsed pre-polarization magnetic module of variable lengths and a control computer for the acquisition and transfer of data, all of which are mutually associated;
   wherein, the magnetic resonance sensor module comprises:
      a device configured to generate a constant and homogeneous magnetic field;
      a radio-frequency exciting/receiving antenna;
      a radio-frequency electronic module for magnetic resonance; and
      a magnetic resonance digital module;
   wherein, the radio-frequency electronic module comprises:
      a transmitter $T_x$, with a plurality of filters, impedance adaptation and blanking circuits;
      a merit factor Q control circuit;
      a receiver $R_x$, with a plurality of receiving channels and a plurality of filters, impedance adaptation and blanking circuits; and
      a plurality of transmission/reception keys.

2. An apparatus configured for the real time and real volume measuring of flow-rate and cuts of the production of a complex fluid according to claim 1, wherein said complex fluid consists of a heterogeneous blend of more than one fluid, even in different phases.

3. An apparatus configured for the real time and real volume measuring of flow-rate and cuts of the production of a complex fluid according to claim 1, wherein said pulsed pre-polarization magnetic module of variable length consists of successive segments, each segment exhibiting a variable length and pulsed action, configured for the selection of fluid components with successive lower values of relaxation times.

4. An apparatus configured for the real time and real volume measuring of flow-rate and cuts of the production of a complex fluid according to claim 1, wherein the magnetic resonance sensor module further comprises a device which generates a steady and homogeneous magnetic field.

5. An apparatus configured for the real time and real volume measuring of flow-rate and cut of the production of a complex fluid according to claim 1, wherein said magnetic resonance digital module bears a single NMR signal sensor and exciting/receiving antenna and its corresponding tuning circuit.

6. An apparatus configured for the real time and real volume measuring of flow-rate and cut of the production of a complex fluid according to claim 5, wherein said NMR signal exciting/receiving antenna is comprised of an exciting antenna and another NMR signal receiving antenna, which are not coupled one to the other, and their respective individual tuning circuits.

7. An apparatus configured for the real time and real volume measuring of flow-rate and cut of the production of a complex fluid according to claim 3, wherein the pulsed pre-polarization module of variable length bears one or a plurality of said segments with permanent magnetic field, each of which may be sequentially approached to or separated from the production duct in order to generate in such duct a pre-polarization pulsed and a magnetic field of variable length.

8. An apparatus configured for the real time and real volume measuring of flow-rate and cut of the production of a complex fluid according to claim 3, wherein from one or a plurality of said segments which generate a localized magnetic field in said production duct, each may be sequentially activated by means of electric currents of variable duration.

9. An apparatus configured for the real time and real volume measuring of flow-rate and cuts of the production of a complex fluid according to claim 4, wherein the magnetic resonance sensor module bears a device configured for neutralizing eventual interferences due to shifts at the resonance frequency, due to changes of the $B_O$ value on account of environmental thermal effects.

10. An apparatus configured for the real time and real volume measuring of flow-rate and cut of the production of a complex fluid, comprising a magnetic resonance sensor module, a pulsed pre-polarization magnetic module of variable length, and a control computer for the acquisition and transfer of data, all of which are mutually associated;
    wherein, the magnetic resonance sensor module comprises:
       a device configured to generate a constant and homogeneous magnetic field;
       a radio-frequency exciting/receiving antenna;
       a radio-frequency electronic module for magnetic resonance; and
       a magnetic resonance digital module;
    wherein, said magnetic resonance digital module comprises:
       a radio-frequency signal generator;
       a pulse generator, said generator providing a plurality of synchronized command pulses;
       a device for the digitalization of the magnetic resonance signal, which device comprises a plurality of receiving/digitalization channels; and
       a plurality of connection interfaces from said control computer to said digital module, said magnetic resonance sensor module and said pre-polarization module.

11. An arrangement configured for the sequential measurement of flow-rate and cut of a complex fluid production in real time and volumes in multiple-component complex fluids production lines that uses an apparatus comprising a magnetic resonance sensor module, a pulsed pre-polarization magnetic module of variable length, and a control computer for the acquisition and transfer of data, all of which are mutually associated;
    wherein, the magnetic resonance sensor module comprises:
       a device configured to generate a constant and homogeneous magnetic field;
       a radio-frequency exciting/receiving antenna;
       a radio-frequency electronic module for magnetic resonance; and
       a magnetic resonance digital module;
    wherein, the radio-frequency electronic module comprises:
       a transmitter $T_x$, with a plurality of filters, impedance adaptation and blanking circuits;
       a merit factor Q control circuit;
       a receiver $R_x$, with a plurality of receiving channels and a plurality of filters, impedance adaptation and blanking circuits; and
    a plurality of transmission/reception keys; and
    wherein, each of said different multiple-component complex fluid production lines bears one of said sensor assemblies.

12. An arrangement configured for the sequential measurement of flow-rate and cut of a complex fluid production in real time and volumes in multiple-component complex fluids production lines that uses, an apparatus comprising a magnetic resonance sensor module, a pulsed pre-polarization magnetic module of variable length, and a control computer for the acquisition and transfer of data, all of which are mutually associated;

wherein, the magnetic resonance sensor module comprises:
- a device configured to generate a constant and homogeneous magnetic field;
- a radio-frequency exciting/receiving antenna;
- a radio-frequency electronic module for magnetic resonance; and
- a magnetic resonance digital module;

wherein, the radio-frequency electronic module comprises:
- a transmitter $T_x$, with a plurality of filters, impedance adaptation and blanking circuits;
- a merit factor Q control circuit;
- a receiver $R_x$, with a plurality of receiving channels and a plurality of filters, impedance adaptation and blanking circuits; and
- a plurality of transmission/reception keys; and wherein, a single sensor assembly is fixedly mounted on said auxiliary line which is connected to a group onto which the various production lines of complex fluid converge and a selection key is activated in order to direct production of each production line onto said auxiliary line.

13. A method of directly measuring in real time and flow-rates of the proportion and flow-rate of different components which form a multiple-component complex fluid, using an apparatus comprising a magnetic resonance sensor module, a pulsed pre-polarization magnetic module of variable length, and a control computer for the acquisition and transfer of data, all of which are mutually associated;

wherein, the magnetic resonance sensor module comprises:
- a device configured to generate a constant and homogeneous magnetic field;
- a radio-frequency exciting/receiving antenna;
- a radio-frequency electronic module for magnetic resonance; and
- a magnetic resonance digital module;

wherein, the radio-frequency electronic module comprises:
- a transmitter $T_x$, with a plurality of filters, impedance adaptation and blanking circuits;
- a merit factor Q control circuit;
- a receiver $R_x$ with a plurality of receiving channels and a plurality of filters, impedance adaptation and blanking circuits; and
- a plurality of transmission/reception keys;

said method comprising the following steps:
a. activating a first segment of the pre-polarization magnetic field in order to pre-polarize resonant nuclei of said multiple-component complex fluid during a time adequate regarding a spin-lattice relaxation time $T_1$ of said first selected component in order to establish proportion and flow-rate thereof;
b. transmitting radio-frequency pulses through a transmitter $T_x$ included in said radio-frequency electronic module, according to the CPMG pulses sequence;
c. emitting said radio-frequency pulses from said radio-frequency electronic module towards said magnetic resonance sensor module in order to excite said resonant nuclei of said complex fluid and generate a magnetic resonance signal (NMR) as a response to said emitted radio-frequency pulses;
d. receiving response signals at said sensor module;
e. emitting said signals in said sensor assembly, through said receiver $R_x$, included in said radio-frequency electronic module;
f. digitalizing said response signals received by an analog/digital converter which is included in said magnetic resonance digital module;
g. sending said digitalized signals to said control computer;
h. activating a second segment of said pre-polarization magnetic field in order to pre-polarize said resonant nuclei of said multiple-component complex fluid during a time appropriate as regards the value of said second shorter spin-lattice relaxation time $T_1$ of said selected second component for the determination of said second component proportion and flow-rate;
i. repeating steps b) to h) in order to obtain adequate signals for further mathematical analysis in order to obtain relative proportions and flow-rates of each of the different components of said complex fluid;
j. activating a third segment of said pre-polarization magnetic field in order to pre-polarize said resonant nuclei of said multiple-component complex fluid during a time appropriate as regards the value of said third shorter spin-lattice relaxation time $T_1$ of said selected third component for the determination of said third component proportion and flow-rate;
k. repeating steps b) to j) in order to obtain adequate signals for further mathematical analysis in order to obtain relative proportions and flow-rates of each of the different components of said complex fluid;
l. repeating steps b) to k) until all of the measurable components are measured; and
m. processing the obtained resonance signals in order to directly measure in real time and flow rates the proportion and flow-rate of each of the components of the complex fluid and presenting values indicative in real time and flow rates the proportion and flow-rate of each of the components of the complex fluid to a user of the apparatus.

14. A method according to claim 13, wherein said sequence of excitation/detection pulses for measuring said velocity of each component of said multiple-component complex fluid is of the CPMG type.

15. A method according to claim 13, wherein said sequence of excitation/detection pulses for measuring said velocity y of each component of said multiple-component complex fluid is of the SSFP type.

16. A method according to claim 13, wherein said sequence of excitation/detection pulses for measuring said velocity of each component of said multiple-component complex fluid is of the CWFP type.

17. A method according to claim 13, wherein said NMR signal may be obtained by means of said procedure of resonant excitation and off-resonance detection, known as "TONROF".

* * * * *